United States Patent [19]

Frank et al.

[11] Patent Number: 4,920,972
[45] Date of Patent: May 1, 1990

[54] GEL-FILLED BLOOD PRESSURE TRANSDUCER

[75] Inventors: Thomas P. Frank, Dublin; Warren B. Nicholson, Worthington; Mark D. Pfouts, Powell, all of Ohio

[73] Assignee: Medex, Inc., Hilliard, Ohio

[21] Appl. No.: 283,224

[22] Filed: Dec. 12, 1988

Related U.S. Application Data

[63] Continuation-in-part of Ser. No. 9,643, Jan. 27, 1987, abandoned.

[51] Int. Cl.$^5$ ............................................. A61B 5/02
[52] U.S. Cl. .................................... 128/675; 128/748; 73/706
[58] Field of Search .............................. 128/672–675, 128/748; 73/706, 708, 715, 721, 723; 29/450, 454

[56] References Cited

U.S. PATENT DOCUMENTS

| | | | |
|---|---|---|---|
| 4,398,542 | 8/1983 | Cunningham et al. | 128/675 |
| 4,576,181 | 3/1986 | Wallace et al. | 128/748 X |
| 4,610,256 | 9/1986 | Wallace | 128/673 X |
| 4,679,567 | 7/1987 | Hanlon et al. | 128/675 |
| 4,686,764 | 8/1987 | Adams et al. | 73/706 X |

Primary Examiner—Angela D. Sykes
Attorney, Agent, or Firm—Wood, Herron & Evans

[57] ABSTRACT

A reusable pressure transducer for use with a detachable dome. The pressure transducer includes a body having a recess with an opening covered by a flexible diaphragm. The body has a hole opposite the flexible diaphragm and a sensor placed over the hole. A dielectric gel fills the recess to transmit to the sensor variations in pressure imparted to the diaphragm.

6 Claims, 1 Drawing Sheet

U.S. Patent     May 1, 1990     4,920,972
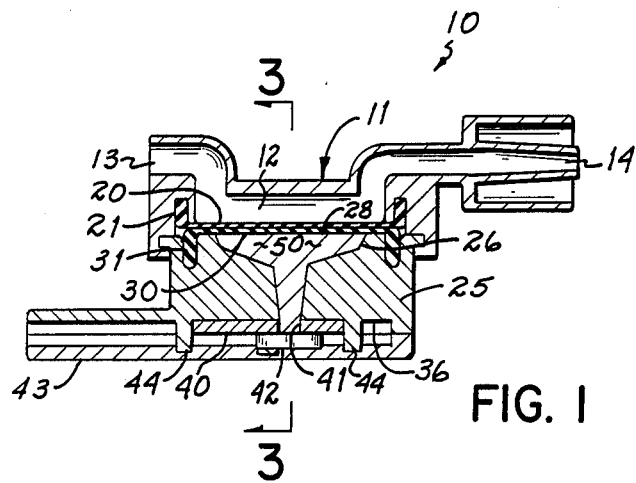
FIG. 1
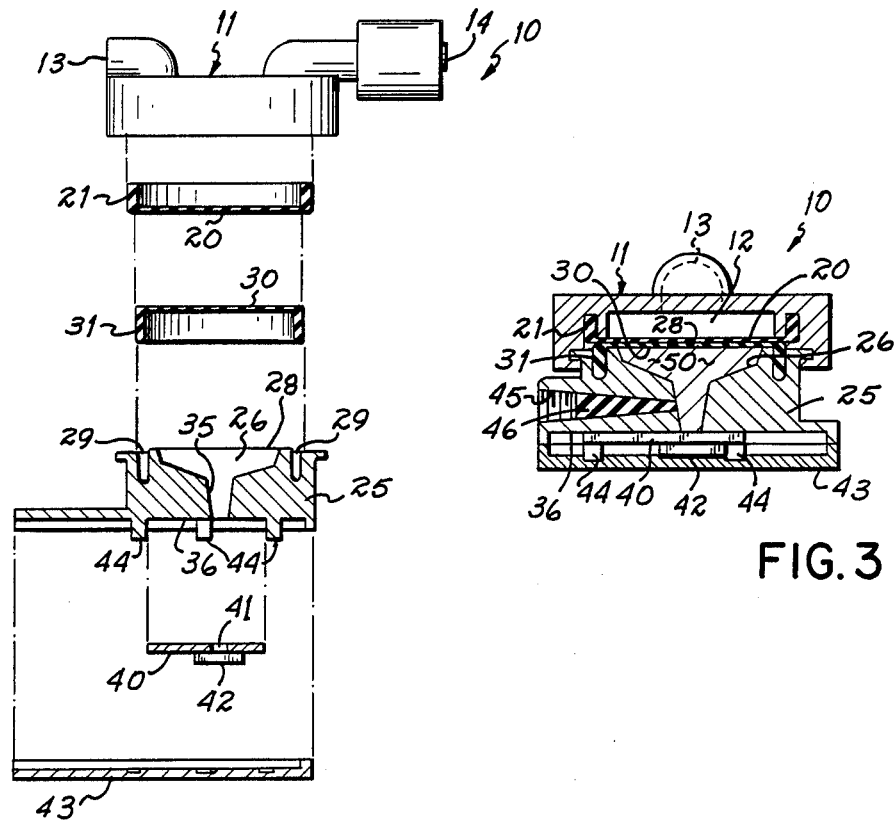
FIG. 3
FIG. 2

GEL-FILLED BLOOD PRESSURE TRANSDUCER

This is a continuation-in-part of application Ser. No. 009,643 filed Jan. 27, 1987, now abandoned.

This invention relates to a reusable transducer and more particularly, to a reusable transducer, for monitoring blood pressure. In continuous real time monitoring of blood pressure, a catheter is inserted into a patient's artery. The catheter is filled with a saline solution to form a static column by which blood pressure is transmitted through the catheter line. The catheter, or a line connected to a catheter, is connected to a transducer that detects pressure variations and transduces them into electrical signals.

Transducers generally are of two types, disposable and reusable transducers. The present invention is concerned with a reusable transducer.

A reusable transducer is in two parts. A disposable dome has a cavity which is connectable to the catheter so that the saline solution in the catheter system fills the dome. The cavity is covered with a flexible diaphragm which flexes with variations in pressure of the fluid in the cavity, thereby reflecting variations in blood pressure.

The reusable transducer has a body containing a recess that is covered by a diaphragm. The dome is connectable to the reusable transducer in such a manner that the two diaphragms overlie one another so that the flexures of the dome diaphragm are transmitted directly to the two transducer diaphragms. The sensing element is a piezoresistive silicon sensor that features four pressure sensitive resistors integral to the silicon chip's diaphragm. The four pressure sensitive resistors are interconnected to a thick film microelectronic circuit used to calibrate and temperature compensate the transducer. The silicon chip's diaphragm constitutes one of the two diaphragms located within the transducer.

The first prior art transducers employed a mechanical linkage connection between diaphragm and sensor to transmit movement of the diaphragm to the sensor. In my copending application, Ser. No. 009,643, there is disclosed a reusable transducer body that is filled with oil, the oil being the medium for transmitting the diaphragm flexures to the sensor. In practice, that transducer has been filled with a silicone oil having a viscosity of 20 cps. In practice, the oil-filled reusable transducer has presented problems. One of the primary advantages of substituting an oil medium for the linkage heretofore used is that the oil provides another layer of dielectric insulation between the electrically-connected sensor and the patient.

The oil has a low viscosity and high mobility. It has a strong tendency to be absorbed by epoxies and adhesives such as the adhesive that holds the silicon chip to the alumina substrate of the sensor. The end effect is a significant and often severe change in the silicon chip's performance.

The low viscosity oil also has a propensity to find any leak paths that might exist within the transducer. Oil leaking out of the transducer causes a reduction in the coupling efficiency between the rubber diaphragm and the silicon chip. This results in reduced transducer sensitivity and a decrease in the balance of the Wheatstone bridge forming part of the sensor circuit. Further, a hole in the diaphragm would result in a failure of the oil-filled transducer. Apply pressure to the oil, as by the blood pressure to be measured, and the process leading to failure is accelerated. This failure can be extremely dangerous because of the time that the transducer's sensitivity is dropping, the clinician will not necessarily note the transducer failure and the patient ma be therapeutically treated for low blood pressure.

BRIEF SUMMARY OF THE INVENTION

An objective of the present invention has been to provide a reusable transducer having the advantages of a fluid medium for transmission of pressure to the sensor while avoiding the disadvantages of the known oil-filled transducer described above.

This objective of the invention is attained by providing, as the medium for transmitting pressure from the diaphragm to the sensor, a highly viscous gel. The gel is so viscous that its viscosity cannot be measured. In the preferred embodiment, the physical condition of the gel is measured by a Universal Penetrometer. The gel has a penetration of 3–9 mm using a 19.5 gram shaft having a one-fourth inch diameter foot.

The advantages are:

The gel will not permeate through small cracks and holes like the oil. The gel acts like a sealant not allowing air into the transducer or gel out of the transducer. This helps alleviate two common problems with oil-filled transducers.

a) Small cracks and holes or poor sealing areas can cause air to be introduced into oil-filled transducers causing a degradation in the transducer performance. Some of the specifications affected by this include frequency response, volumetric displacement and offset.

b) Small cracks and holes or poor sealing areas can cause oil to leak out of the transducer causing possible cleanliness problems in clinical situations while degrading the performance, as mentioned above.

The gel will not prematurely deteriorate the RTV adhesive used in the pressure sensor assembly.

Gel-filled units have lower volumetric displacement and higher resonant frequency that oil-filled units.

It is another feature of the invention that the gel is formed in situ, that is, two uncured parts each having a viscosity of about 400 cps are mixed in a vacuum to remove air. Before the mixture cures, the mixture is introduced through a closable port in the transducer body by means of a syringe, while the body is maintained in a vacuum. Again, before curing, the mixture is free-flowing and totally fills the chamber with all air removed by virtue of the vacuum process. The filling port is closed. Thereafter, the gel is cured through time and temperature and has the almost solid quality described above. The gel is sufficiently mobile to transmit pressure variations from the diaphragm that it contacts to the sensor. It simply will not flow, however, and therefore totally eliminates the problem of leakage as well as migration of the oil which can disbond or loosen the cured adhesive between the silicon chip and the substrate.

BRIEF DESCRIPTION OF THE DRAWINGS

The several features of the present invention will become more readily apparent from the following detailed description taken in conjunction with the accompanying drawings in which:

FIG. 1 is a cross-sectional view of the invention;

FIG. 2 is a disassembled view of the invention partly in section; and

FIG. 3 is a cross-sectional view taken along lines 3—3 of FIG. 1.

DESCRIPTION OF THE PREFERRED EMBODIMENTS

As shown in the drawings, the transducer 10 is, in operation, connected to a dome 11. The dome 11 has a cavity 12 and two passageways 13 and 14 that communicate with the cavity 12. Passageway 13 is connected to a catheter. Passageway 14 is connected to a saline solution supply, the saline solution filling all of the passageways and the cavity 12 up to the patient's blood vessel. Thus, there is a column of fluid directly from the patient's blood vessel to the cavity. That column of fluid will directly reflect the variations in the patient's blood pressure. The cavity 12 is closed by a rubber diaphragm 20 having a rim 21 imparting a cup-shaped configuration to the diaphragm. The rim 21 is seated and sealed in an annular channel in the dome so as to confine the saline solution in the cavity 12. The diaphragm 20 is in direct contact with the saline solution and, hence, will expand and contract with variations in the blood pressure of the patient.

The reusable transducer 10 has a body 25 having a cavity 26. The cavity 26 has a large opening 28 at one side of the body 25. An annular channel 29 surrounds the opening 28. A cup-shaped nitrile rubber diaphragm 30 having a rim 31 is disposed over the opening 28 with the rim 31 being sealed in the channel 29 to provide an air and liquid-tight seal of the diaphragm with respect to the body.

The body has a tapered bore 35 extending from the cavity 26 to the lower surface 36 of the body. An alumina substrate 40 is adhesively secured to the surface 36 of the body 25 and covers the bore 35. The substrate itself has a hole 41 which, when the substrate is adhesively-secured to the body, communicates with the bore 35. A silicon chip 42 has a pressure-sensitive diaphragm, such as that found on piezoresistive type sensors, that is connected by electrical circuits into a Wheatstone bridge. Other circuit components, including temperature compensation circuit, if necessary, are printed on the alumina substrate. Plastic tabs 44 surround the substrate projecting from the surface 36 to provide positioning elements for the proper location of the substrate on the surface of the body. The substrate is protected by a bottom cap which is secured to the lower surface.

As shown in FIG. 3, the body has still another bore 45 in the side of the body that communicates with the tapered bore 35. The bore 45 is provided for the purpose of filling the cavity 26 with a gel-forming fluid indicated at 50.

In order to fill the body with the fluid 50, the following procedure is carried out.

The fluid 50 initially has two parts, A and B. These parts are the system Visilox V-191 of Visilox Systems, Inc., Troy, N.Y. Part A is a polydimethylsiloxane and includes a platinum catalyst. Part B is also polydimethylsiloxane with a methyl hydrogen cross linker. When the gel is formed, it is a clear, very soft silicone material having the following properties:

| | |
|---|---|
| PENETRATION, mm (Universal Penetrometer, 19.5 gm shaft, ¼ inch diameter foot) | 3.0-9.0 |
| OPERATING TEMP. RANGE | −55° C. to +200° C. |
| LINEAR COEFFICIENT OF EXPANSION (in/in/°C.) | $3.0 \times 10^{-4}$ |
| TEMPERATURE EFFECT ON VOLUME INCREASE/10°C. | Approx. 1% |
| THERMAL CONDUCTIVITY (cal)(cm)/(sec)(cm²) (°C.) | $3.5 \times 10^{-4}$ |
| LINEAR SHRINKAGE, % | 0.1 |
| DIELECTRIC STRENGTH, volts/mil | 500 |
| DIELECTRIC CONSTANT, 1 KHz | 2.8 |
| DISSIPATION FACTOR, 1 KHz | 0.001 |
| VOLUME RESISTIVITY, ohm-cm | $1.3 \times 10^{15}$ |
| SODIUM ION CONTENT, ppm | 2 |
| POTASSIUM ION CONTENT, ppm | 4 |

Before cured, both parts A and B have a viscosity of 400 cps. In the process of filling the cavity 50, equal parts of A and B are poured together in a container. A magnetic stirring rod is placed in the container. The container is placed on a stirring plate and turned on. The stirring plate is placed in a vacuum chamber so that during the stirring, or mixing, all of the air is evacuated from the liquid.

The liquid is slow to cure. At room temperature, cure time is approximately 24 hours. While still liquid, the mixture is placed in a syringe and the syringe is used to introduce the mixture through the bore 45 into the cavity 26 so as to fill the cavity 26, the tapered bore 35, the hole 41 in the substrate 40 and a portion of the bore 45. Those steps are performed in a vacuum to assure the exhaustion of all of the air in the cavity and replacing it with the gel. A plug 46 is then introduced into the bore 45 to seal the bore 45 off. The amount of liquid in the bore 45, after filling, is sufficiently great that upon introduction of the plug, a portion of it must be pushed toward the cavity, thereby causing a slight distention or stressing of the diaphragm 30. This feature of the invention assures the complete filling of the cavity and elimination of any air. The slightly distended diaphragm will have a good fit with the diaphragm 20 of the dome 11.

The thus totally filled and closed body 25 is heated for four hours at 65° C. (150° F.) to cure the mixture and create the gel having the properties listed above.

The gel will not permeate through small cracks and holes in the body. Rather, the gel acts like a sealant, not allowing air in the cavity or gel out of the cavity.

The gel will not prematurely deteriorate the RTV adhesive used in the pressure sensor assembly. The gel-filled units have a lower volumetric displacement and higher resonant frequency than oil-filled units. Finally, the gel-filled units perform better over time. After 70,000,000 pressure cycles, representing approximately 400 days of use, the transducer's sensitivity change was seven times less on gel-filled units than oil-filled units.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof;

We claim:

1. A reusable pressure transducer comprising:
   a body having a recess terminating in an opening surrounded by a rim, said body having an outer surface;
   a flexible diaphragm placed over said rim to enclose said recess;
   said body having a hole spaced from said diaphragm, said hole connecting the outer surface of said body to said recess;

a pressure sensor mounted on said outer surface over said hole;

and a dielectric gel completely filling said recess and hole and in contact with both said diaphragm and said pressure sensor whereby pressure on said diaphragm will be communicated through said gel to said sensor, said dielectric gel slightly distending said diaphragm.

2. A reusable pressure transducer as in claim 1 in which said gel is cured in said recess from two parts that are mixed together:

one of said parts is polydimethylsiloxane and a catalyst, and the other of said parts is polydimethylsiloxane with a hydrogen cross linker.

3. The method of making a transducer comprising the steps of:

forming a body with a cavity opening at one side and a first bore extending from said cavity to another side of said body;

forming a filling bore to said cavity;

enclosing said opening with a flexible diaphragm;

mounting a sensor assembly over said first bore;

filling said cavity with a curable liquid through said filling bore;

plugging said filling bore, the quantity of liquid in said cavity distending said diaphragm upon plugging of said filling bore; and curing said liquid to form a gel.

4. The method as in claim 3 further comprising the steps of:

mixing said curable liquid in a vacuum;

filling said cavity with said liquid while said cavity is in a vacuum.

5. The method as in claim 4 in which one part of said gel is polydimethylsiloxane and a platinum catalyst and the other part is polydimethylsiloxane with a hydrogen cross linker.

6. The method as in claim 3 in which said gel has a Universal Penetrometer penetration of about 3.0 –9.0 mm using a 19.5 gram shaft with a ¼ inch diameter foot.

* * * * *